United States Patent [19]

Pierschbacher et al.

[11] Patent Number: 4,589,881

[45] Date of Patent: May 20, 1986

[54] POLYPEPTIDE

[75] Inventors: Michael D. Pierschbacher, San Diego; Erkki I. Ruoslahti, Olivenhain, both of Calif.

[73] Assignee: La Jolla Cancer Research Foundation, La Jolla, Calif.

[21] Appl. No.: 518,036

[22] Filed: Jul. 28, 1983

Related U.S. Application Data

[63] Continuation-in-part of Ser. No. 405,239, Aug. 4, 1982, Pat. No. 4,517,686, and a continuation-in-part of Ser. No. 433,457, Oct. 8, 1982, abandoned.

[51] Int. Cl.[4] ........................ A61F 1/00; A61K 37/00; C07C 103/52; C07G 7/00

[52] U.S. Cl. ........................................ 623/11; 623/66; 128/1 R; 260/112.5 R; 530/350; 530/815

[58] Field of Search ............ 3/1, 1.4; 128/1 R, 334 R; 260/112.5 R; 424/177; 623/1, 71, 66 A, 66 B

[56] References Cited

PUBLICATIONS

Pierschbacher et al.; "The Cell Attachment . . . "; The Journal of Bio. Chem.; vol. 257, No. 16, pp. 9593–9595; 8/25/82.

Petersen et al.; "Partial Primary Structure . . . "; Proc. Natl. Acad. Sci.; vol. 80, pp. 137–141; 1/1983.

Hynes, et al., Cell Surface Fibronectin and Oncogenic Transformation, *J. Supramolecular Structure*, 11:95–104, 1979.

Hahn, et al., Isolation and Biological Characterization of Active Fragments of the Adhesive Glycoprotein Fibronectin, *Cell*, 18:1043–1051, 1979.

Sekiguchi, et al., Functional Domain Structure of Fibronectin, *Proc. Natl. Acad. Sci.*, 77:2661–2665, 1980.

Grinnell, Frederick, et al., Distribution of Fibronectin during Wound Healing in Vivo., *J. Invest. Dermatol.*, 76:181–189, 1981.

McDonagh, R. P., et al., Amino Acid Sequence of the Factor $XIII_a$ Acceptor Site in Bovine Plasma Fibronectin, *Febs Letters*, 127:174–178, 1981.

Ruoslahti, Erkki, et al., Alignment of Biologically Active Domains in the Fibronectin Molecule, *J. Biol. Chem.*, 256:7277–7281, 1981.

Pande, Hema, et al., Comparative Structural Studies of Human Plasma and Amniotic Fluid Fibronectins, *Bioch. Biophy. Res. Comm.*, 101:265–272, 1981.

Pande, Hema, et al., $NH_2$–Terminal Sequences of DNA–, Heparin–, and Gelatin–Binding Tryptic Fragments from Human Plasma Fibronectin, *Arch. Bioch. Biophy.*, 213:258–265, 1982.

Seitz, T. L., et al., Effect of Fibronectin on the Adhesion of an Established Cell Line to a Surface Reactive Biomaterial, *J. Biomed. Mat. Res.*, 16:195–207, 1982.

(List continued on next page.)

*Primary Examiner*—Richard J. Apley
*Assistant Examiner*—Gregory Beaucage
*Attorney, Agent, or Firm*—Fulwider, Patton, Rieber, Lee & Utecht

[57] ABSTRACT

A polypeptide having the cell-attaching activity of fibronectin. The polypeptide has 108 amino acid residues and the formula: H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-T r-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH. The polypeptide or a biologically active fragment thereof, such as H-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH can be employed in the preparation of substrata designed for the attachment of cells thereto. A Cys-residue may optionally be attached at the C-terminus. It can be linked to the surface of a prosthetic device to particularly attract endothelial cells and fibroblastic cells.

11 Claims, 3 Drawing Figures

PEPTIDE I

ILE-GLY-GLN-GLN-SER-THR-VAL-SER-ASP-VAL-PRO-ARG-ASP-LEU-GLU-VAL-VAL-ALA-ALA-THR-PRO-THR-SER-LEU-LEU-ILE-SER-TRP-ASP-CYS

PEPTIDE II

SER-TRP-ASP-ALA-PRO-ALA-VAL-THR-VAL-ARG-TYR-TYR-ARG-ILE-THR-TYR-GLY-GLU-THR-GLY-GLY-ASN-SER-PRO-VAL-GLN-GLU-PHE-THR-VAL-CYS

PEPTIDE III

PHE-THR-VAL-PRO-GLY-SER-LYS-SER-THR-ALA-THR-ILE-SER-GLY-LEU-LYS-PRO-GLY-VAL-ASP-TYR-THR-ILE-THR-VAL-TYR-ALA-VAL-THR-CYS

PEPTIDE IV

TYR-ALA-VAL-THR-GLY-ARG-GLY-ASP-SER-PRO-ALA-SER-SER-LYS-PRO-ILE-SER-ILE-ASN-TYR-ARG-THR-GLU-ILE-ASP-LYS-PRO-SER-GLN-MET-CYS

OTHER PUBLICATIONS

Vibe-Pedersen, Karen, et al., Amino Acid Sequence of a Peptide from Bovine Plasma Fibronectin Containing a Free Sulfhydryl Group (Cysteine), *Febs. Letters,* 142:26-30, 1982.

Sekiguchi, Kiyotoshi, et al., Monoclonal Antibodies Directed to Two Different Domains of Human Plasma Fibronectin: Their Specificities, *Fed. Eur. Bich. Soc.,* 142:243-246, 1982.

Ehrismann, Ruth, et al., Arrangement of Attachment--Promoting, Self-Association, and Heparin-Binding Sites in Horse Serum Fibronectin, *J. Biol. Chem.,* 257:7381-7387.

Clark, Richard A. F., et al., Fibronectin is Produced by Blood Vessels in Response to Injury, *J. Exp. Med., 156:646-651, 1982.*

Hynes, Richard O., et al., Fibronectins: Multifunctional Modular Glycoproteins, *J. Cell. Biol.,* 95:369-377, 1982.

Petersen, Torbene, et al., Partial Primary Structure of Bovine Plasma Fibronectin: Three Types of Internal Homology, *Proc. Natl. Acad. Sci.,* 80:137-141, 1983.

Frederick Grinnell, Cell Attachment and Spreading Factors, in *Growth and Maturation Factors,* (Dr. Gordon Guroff, Ed.) John Wiley & Sons, Inc., 1983.

Grinnell, Frederick, The Role of Fibronectin in the Bioreactivity of Material Surfaces in Biocompatible Polymers, Metal, and Composites, (Ed. Michael Szycher), Technomic Publishing, Lancaster, Pennsylvania, 1983.

Hayashi, Masao, et al., Domain Structure of the Carboxyl-Terminal Half of Human Plasma Fibronectin, *J. Biol. Chem.,* 258:3332-3340, 1983.

Kornblihtt, Alberto R., et al., Isolation and Characterization of cDNA Clones in Human and Bovine Fibronectins, *Proc. Natl. Acad. Sci.,* 80:3218-3222, 1983.

Peptide I

Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Cys

Peptide II

Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Cys

Peptide III

Phe-Thr-Val-Pro-Gly-Ser-Lys-Ser-Thr-Ala-Thr-Ile-Ser-Gly-Leu-Lys-Pro-Gly-Val-Asp-Tyr-Thr-Ile-Thr-Val-Tyr-Ala-Val-Thr-Cys

Peptide IV

Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-Cys

FIGURE I

Fig. 2
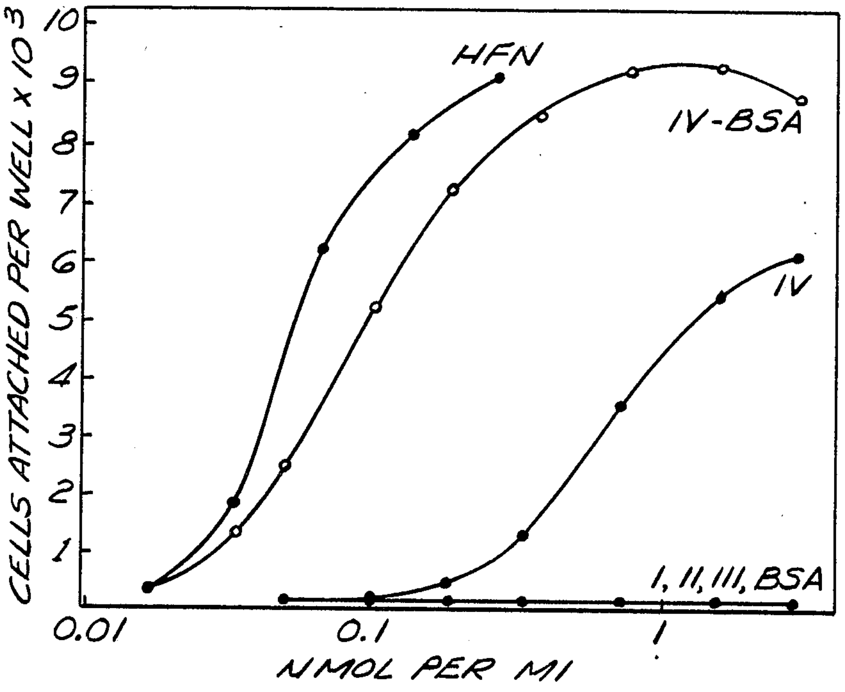
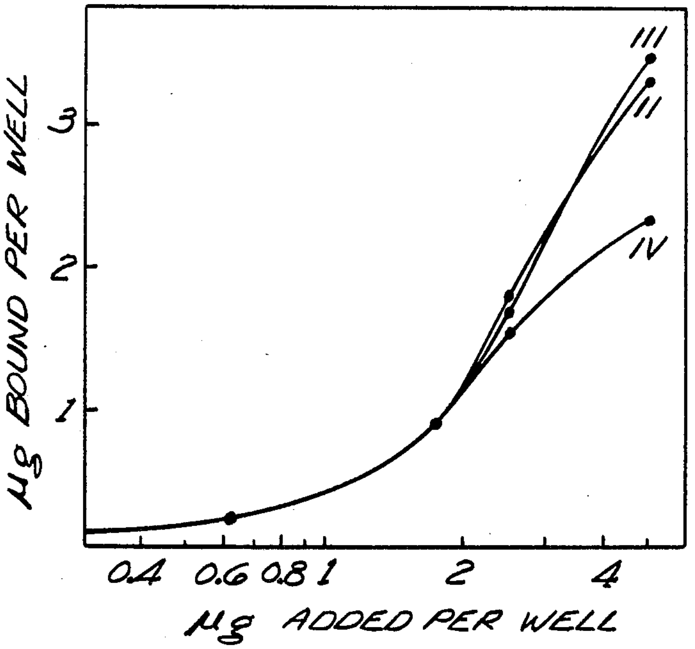
Fig. 3

POLYPEPTIDE

This application is a continuation-in-part of our earlier applications Ser. No. 405,239 filed Aug. 4, 1982 now U.S. Pat. No. 4,517,686 and Ser. No. 433,457 filed Oct. 8, 1982 now abandoned.

This invention is directed to polypeptides related to fibronectin and more particularly to a polypeptide segment of human plasma fibronectin which interacts with cell surfaces and promotes attachment thereto.

BACKGROUND OF THE INVENTION

Fibronectin is a large glycoprotein, about 450 thousand daltons, which is composed of several apparently independent functional domains. Fibronectin was earlier discovered as a major extracellular matrix protein, and it was demonstrated that it would interact in vitro with other structural molecules, such as collagen, glycosaminoglycans, proteoglycans, fibrinogen, fibrin, and actin, as well as with cell surfaces. It was discovered that fibronectin promotes the attachment of suspended cells to collagen and also that it promotes the attachment of suspended cells directly to tissue culture substrate, independent of its binding to collagen. Accordingly, investigation continued with respect to the region of the fibronectin molecule that interacts with cell surfaces.

SUMMARY OF THE INVENTION

A polypeptide fragment of fibronectin which embodies the cell-attachment-promoting activity of fibronectin has now been isolated, purified and characterized as a 11.5 kDal polypeptide having the formula: H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-T r-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH. This polypeptide has 108 amino acid residues, and it or a fragment thereof, which has cell attachment biological activity, can be used to prepare substrata to which cells will attach. Such substrata is useful in cell culture dishes and is also useful for employment in medical prosthetic devices for implantation in the human body that will attract a certain type of cell to a surface.

DESCRIPTION OF THE DRAWINGS

FIG. 1 depicts four synthetic peptides designed after the known sequence of the 11.5 kDal fragment of fibronectin that induces cell attachment. The peptides correspond to residues from cleavage of the natural peptide fragments. The lines indicate amino acids common to two peptides.

FIG. 2 is a graph depicting the attachment of normal rat kidney (NRK) cells to polystyrene microtiter wells coated with human fibronectin (HFN) or synthetic peptides. In each well 10 cells were cultured for 1 hr and those cells that attached were counted. Fibronectin and peptides I, II, III, and IV were assayed both when adsorbed directly to the polystyrene and when coupled to albumin (BSA). Albumin (BSA) alone was also tested. The number of moles of fibronectin was calculated by using the molecular mass of one sub-unit (240 kDal). Cells attach to wells containing fibronectin and peptide IV, but not to wells containing the other peptides or albumin alone.

FIG. 3 is a graph depicting the binding of I-labeled peptides II, III, and IV to plastic microtiter wells. The amount of peptide bound in each well was calculated from the specific radioactivity of each peptide.

DETAILED DESCRIPTION OF THE PREFERRED EMBODIMENTS

The nomenclature used to define the polypeptide is that specified by Schroder & Lubke, "The Peptides", Academic Press (1965) wherein, in accordance with conventional representation the N-terminus appears to the left, and the C-terminus appears to the right. Where the amino acid residue has isomeric forms, it is the L-form of the amino acid that is represented.

The invention provides a polypeptide having the following formula: H-Ile-Gly-Gln-Gln-Ser-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyr-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-T r-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH and is intended to include fragments of the foregoing which have the same cell attachment activity, for example, the synthetic fragment H-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH. Shorter fragments which have the same cell attachment activity as the above fragments are also useful to provide surfaces to which cells will attach and are included in this invention. Moreover, the coupling of the peptide to surfaces may be facilitated in certain instances, without affecting the cell-attachment promoting activity, by adding a Cys residue at the C-terminus.

The polypeptide, or a fragment thereof, can be synthesized by any suitable method, such as by exclusively solid-phase techniques, by partial solid-phase techniques, by fragment condensation or by classical solution addition. Moreover, synthesis may be carried out by recently developed recombinant DNA techniques.

Common to chemical syntheses of peptides is the protection of the labile side-chain groups of the various amino acid moieties with suitable protecting groups which will prevent a chemical reaction from occurring at that site until the group is ultimately removed. Usually, also common is the protection of an alpha-amino group on an amino acid or a fragment while that entity reacts at the carboxyl group, followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The peptides are preferably prepared using solid phase synthesis, such as that described by Merrifield, *J. Am. Chem. Soc.*, 85, 2149 (1964), although other equivalent chemical syntheses known in the art, as mentioned above, can also be used. Solid-phase synthesis is commenced from the C-terminus of the peptide by coupling a protected alpha-amino acid to a suitable resin, as generally set forth in U.S. Pat. No. 4,244,946, issued Jan. 21, 1982 to Rivier et al., the disclosure of which is incorporated herein by reference. Examples of syntheses of this general type are set forth in U.S. Pat. Nos. 4,305,872 and 4,316,891. Discussion of the solid-phase synthesis of a 41-residue polypeptide is set forth in *Science*, 213, 1394–1397 (September 1981) in an article by Vale et al., which refers to a more detailed discussion of the synthesis, which appears in an article by Marki et al. in *J. Am. Chem. Soc.*, 103, 3178 (1981).

In synthesizing the polypeptide, Met having its alpha-amino group suitably protected is coupled to a chloromethylated polystyrene resin or the like. The methylthiol side-chain may optionally also be protected or it may be left unprotected. If Cys is employed at the C-terminus, it is coupled instead to the resin after protecting its alpha-amino group and its sulfhydryl side-chain. After removal of the alpha-amino protecting group, as by using trifluoroacetic acid in methylene chloride, the next step in the synthesis is ready to proceed. Other standard cleaving reagents and conditions for the removal of specific amino protecting groups may be used, as described in "The Peptides" identified hereinbefore.

The remaining alpha-amino and side-chain protected amino acids are then coupled stepwise in the desired order to obtain an intermediate compound connected to the resin. As an alternative to adding each amino acid separately in the synthesis, some of them may be coupled to one another prior to the addition to the solid-phase reactor. The selection of the appropriate coupling reagents is within the skill of the art.

After the desired amino acid sequence has been completed, the intermediate peptide is removed from the resin support by treatment with a reagent, such as liquid HF, which not only cleaves the peptide from the resin, but also cleaves all the remaining side-chain-protecting groups. The polypeptide can then be purified by gel permeation followed by semipreparative HPLC, as described in Rivier et al., *Peptides: Structure and Biological Function* (1979) pp. 125–128. A purity of at least 93% or higher (based upon all peptides present) is reasonably obtainable and is preferred for clinical testing and/or use. A purity as high as about 98% is practical; however, for certain in vitro applications, lower purity may be acceptable. Accordingly, the polypeptide is considered particularly useful when it is in substantially pure form which, for purposes of this application, means at least about 50 weight percent, based upon all peptides present.

EXPERIMENTAL-I

Materials and Methods

The cell attachment domain of fibronectin was purified as described earlier (Pierschbacher, M. D. et al, (1981) *Cell* 26, 259–267). Molecular weight estimation was done by sodium dodecyl sulfate polyacrylamide gel electrophoresis using a concentration gradient of polyacrylamide from 10 to 20%, and by ultracentrifugation. The centrifugation was performed in an MSE Centriscan (TM) analytical ultracentrifuge equipped with a six-place aluminum rotor. The low speed equilibrium sedimentation method was applied with 3 mm columns in 1 cm single sector cells. The partial specific volume was calculated from the amino acid composition.

Fragmentation Methods

Cleavage at methionine residues was attempted with a 100-fold molar excess of cyanogen bromide in 70% formic acid.

Acid cleavage at aspartyl bonds was done in dilute hydrochloric acid, pH 2.0, in a sealed evacuated tube, at 110 C. for 2 h. The sample was then lyophilized.

Cleavage at tryptophan residues was achieved by treatment of the protein with a several thousand fold molar excess of cyanogen bromide in equal volumes of 88% formic acid and heptafluorobutyric acid.

*Syaphylococcus aureus* V8 protease (Miles, Elkhart, IN) digestion was carried out in 0.1 M ammonium bicarbonate containing 0.1% sodium dodecyl sulfate, for 19 h at 37 C., using an enzyme to substrate ratio of 1:50 (w/w).

Thermolysin (TM) (Calbiochem, La Jolla, CA) digestion was done in 0.1 M ammonium bicarbonate containing 5 mM calcium chloride for 1 h at 45 C. at an enzyme to substrate ratio of 1:100 (w/w). The digestion was stopped by adding EDTA.

Carboxypeptidase A digestion was carried out by treating the cell attachment fragment, dissolved in 0.1 M ammonium bicarbonate containing 0.1% sodium dodecyl sulfate, with carboxypeptidase A (Sigma, St. Louis, MO) at an enzyme to substrate ratio of 1:500 (w/w). At various time points, aliquots were taken out, and the reaction was stopped by adding acetic acid to a final concentration of 50%. These samples were then lyophilized, and analyzed for free amino acids. A blank digest without substrate, was run in parallel.

Purification of peptides

Gel chromatography on Sephadex G-75 (TM) superfine or Sephacryl S-200 (TM) (Pharmacia A.B., Uppsala, Sweden) was used as the initial purification step. The G-75 column was equilibriated and eluted with 0.1 M ammonium bicarbonate and the S-200 column with 6 M guanidine hydrochloride. Further purification was achieved by reverse-phase liquid chromatography on a μ-Bondapak $C_{18}$-column (TM) (Waters [Millford, MA] dual pump gradient chromatography system). A 60 min linear gradient of 0–80% ethanol in 0.1 M ammonium bicarbonate was used for elution of peptides, which were monitored by absorbance at 230 nm using an LDC Spectromonitor III (TM) variable wave length detector.

Amino acid analysis

Peptides were hydrolyzed at 110° C. for 24 h in 6 N hydrochloric acid, containing 0.1% phenol, and analyzed on a Beckman (TM) 121 M amino acid analyzer (Tragardh, L, et al. (1970) Biochemistry 18, 2218–2226). Values for serine and threonine were corrected for losses during hydrolysis using standard correction factors or, in the case of the intact cell attachment fragment, by linear extrapolation to zero time using 24, 48, and 72 h hydrolysis times. Tryptophan was determined spectrophotometrically. Performic acid oxidation was used for the determination of cysteine as cysteic acid.

Amino acid sequence analysis

Automated Edman degradation was performed on a Beckman (TM) 890 C sequencer using the Beckman 122974 fast protein Quadrol (TM) program. The Quadrol concentration was 0.5 M. Identification and quantitation of amino acid phenylthiohydantoins were done by high preformance liquid chromatography (hplc).

RESULTS

Amino-terminal amino acid sequence

Automated amino acid sequence analysis of intact cell attachment domain allowed unambiguous identification of the first 50 residues.

Chemical fragmentation

Treatment of the cell attachment fragment with dilute hydrochloric acid for cleavage at aspartyl bonds resulted in several peptides, some of which were insoluble after lyophilization. Those peptides soluble in 0.1 M ammonium bicarbonate were fractionated on a column of Sephadex G-75 (TM) into one major and four minor peaks. Amino acid composition data and sequence analysis of the A2 peptide allowed identification of residues 87 through 107. The portion insoluble in 0.1 M ammonium bicarbonate was dissolved in 6 M quanidine hydrochloride and fractionated on a column of Sephacryl S-200 (TM) (Pharmacia AB, Sweden) equilibriated with 6 M guanidine hydrochloride. This allowed the isolation of a 57 residue peptide (fragment A1), and 53 cycles of automated Edman degradation yielded the amino acid sequence of residues 30 through 83 of the cell attachment fragment.

One fragment was purified to homogeneity from the tryptophan-directed cyanogen bromide cleavage. Amino acid analysis showed it to be the amino-terminal 28 residues of the whole cell attachment fragment. Automated sequence analysis confirmed the amino acid sequence of this region of the fragment.

The amino acid composition of the intact cell attachment fragment and the other peptides derived from it by chemical fragmentation are listed in the following table. Minor contaminants in fraction A2 resulted in some discrepancy between amino acid composition data and the actual number of residues found. Good yields in the automated sequences analysis as well as extensive overlaps with other peptides, however, make the sequence of this peptide unambiguous.

TABLE I

Amino acid compositions of peptides derived from chemical cleavage of cell attachment fragment; the integral values in parenthesis are based on the sequence

| | Acid cleavage | | Trp cleavage | |
|---|---|---|---|---|
| Amino acid | A1 | A2 | W1 | Intact cell attachment fragment |
| Lys | 2.1 (2) | 1.0 (2) | | 3.9 (4) |
| His | | | | 0 (0) |
| Arg | 2.9 (3) | 1.0 (1) | 1.0 (1) | 5.0 (5) |
| Cys | | | | 0[b] (0) |
| Asp | 2.6 (3) | 2.2 (2) | 2.2 (2) | 8.1 (8) |
| Thr | 8.4 (9) | 1.8 (1) | 3.0 (3) | 12.7[c] (13) |
| Ser | 4.5 (4) | 3.9 (5) | 3.7 (4) | 12.8[c] (13) |
| Glu | 3.4 (3) | 2.0 (2) | 3.0 (3) | 8.4 (8) |
| Pro | 4.5 (4) | 2.4 (3) | 1.9 (2) | 8.8 (9) |
| Gly | 7.2 (8) | | 1.2 (1) | 8.9 (9) |
| Ala | 3.9 (4) | 1.8 (1) | 1.8 (2) | 7.7 (8) |
| Val | 6.9 (7) | 1.5 (0) | 3.2 (4) | 10.5[d] (11) |
| Met | | 0.6 (1) | | 1.1 (1) |
| Ile | 3.1 (3) | 3.9 (3) | 1.8 (2) | 7.7[d] (8) |
| Leu | 1.5 (1) | 1.9 (0) | 2.9 (3) | 4.3[d] (4) |
| Tyr | 4.5 (5) | 1.0 (1) | | 6.1 (6) |
| Phe | 1.1 (1) | | | 1.1 (1) |
| Trp | | | [a](1) | 0.9 (1) |
| Total | 57 | 22 | 28 | 108 |
| Position | 30–86 | 87–108 | 1–28 | — |
| Yield (%) | 13 | 90 | 38 | — |

[a] oxidized product detected in ultraviolet spectrum of peptide.
[b] performic acid oxidized sample did not yield cysteic acid.
[c] values obtained by linear extrapolation to zero time.
[d] 72 h value only.

Treatment with cyanogen bromide for cleavage at methionine did not result in any detectable fragmentation, indicating that the single methionine residue was located at, or very close to the carboxy-terminus, since no methionine was found in the amino-terminal sequence.

Enzymatic digestions

Carboxypeptidase A digestion of whole cell attachment fragment released one mole of methionine per mole of protein in five minutes, which established this amino acid as the carboxy-terminal residue.

Two small peptides were isolated from the *S. aureus* V8 protease digestion after Sephadex G-75 chromatography. From their amino acid compositions it was evident that they originated from the amino- and carboxy-terminal parts of the molecule, respectively. Amino acid sequence analysis confirmed the sequence of the carboxy-terminal portion of the acid cleavage fragment.

A number of peptides were isolated from the thermolytic digest by chromatography on Sephadex G-75 (TM) followed by high performance liquid chromatography.

The amino acid sequence data of the thermolytic peptides confirmed the data obtained from the other sequenced peptides.

It is known that the entire polypeptide exhibits the desired biological activity as measured by cell-attachment activity, and that certain fragments of the polypeptide will also exhibit substantially the same cell-attaching activity. Accordingly, those biologically active fragments of the 108-amino-acid-residue polypeptide are considered as constituting part of the invention, e.g. the 30-residue fragment at the C-terminus, which has been synthesized, tested and found to exhibit the same activity as the entire sequence. The entire polypeptide or a biologically active fragment, either with or without a Cys-residue at the C-terminus, can be used as a cell-attachment protein to provide substrata to which cells will attach by using it to treat a surface. Surfaces of synthetic plastic resin materials, for example a cellulose ester such as nitrocellulose, or a comparable material can be treated with the polypeptides of this invention to ensure cell attachment. A similar substratum for cell attachment can be generated by coupling the polypeptide covalently to a solid support, for example glass or a synthetic plastic resin or a long chain polysaccharide, such as agarose, containing a reactive group that can bind the polypeptide. This approach has been proven by coupling the peptide, as well as the synthetic 30-residue fragment, to cyanogen bromide-activated agarose beads (sold under the trademark Sepharose by Pharmacia Fine Chemicals, Uppsala, Sweden), sterilizing the beads by autoclaving and thereafter showing that the polypeptide-coating induces attachment of cells to the beads in a concentration greater than can be obtained by passive absorbtion.

To define further the structure of the cell attachment site four synthetic peptides were designed. Each sequence containing sequences of 29 or 30 amino acids from the 11.5-kDal fragment and together constituting this entire region. Using these peptides, it was demonstrated that the COOH terminal 30 amino acids account for the cell attachment activity of the 11.5-kDal cell adhesive fragment of fibronectin.

EXPERIMENTAL II

Materials and Methods

Source of Peptides. Human fibronectin was obtained from freshly drawn plasma by using gelatin-Sepharose chromatography as described. The 11.5-kDal peptide was isolated from a peptic digest of fibronectin. Four peptides were synthesized chemically by using the Merrifield solid-phase procedure; the synthesis was performed according to specifications given to Peninsula Laboratories (San Carlos, CA). The design of the synthetic peptides was such that each sequence follows the amino acid sequence of the 11.5-kDal cell attachment fragment and has three or four amino acids in common with the adjacent peptide(s). Each peptide has a sequence of 29 or 30 amino acids from the 11.5-kDal fragment plus a cysteine residue at the COOH terminus to facilitate coupling of the peptide to solid phases. The composition of the peptides was verified by amino acid analysis. The peptides are numbered with Roman numerals, starting from the $NH_2$ terminus of the 11.5kDal fragment (See FIG. 1).

Binding of Peptides to Polystyrene. The four synthetic peptides were tested for cell attachment activity in plastic culture dishes as follows: One milligram of each peptide was dissolved in 6 M urea at a concentration of 2 mg/ml at pH 8.0 and reduced by adding dithiothreitol to a final concentration of 45 mM. The peptide was then freed of these reactants by passing it through a 5-ml Sephadex G-25 column equilibrated with phosphate-buffered saline. The fractions containing the peptide were collected and pooled and used in the cell attachment assays. Wells in untreated polystyrene microtiter plates were either left uncoated or coated with bovine serum albumin (hereafter referred to as albumin) by incubating a 20 μg/ml solution in the wells for 2 hr at room temperature. After washing the wells to remove unattached protein, the albumin coating was first derivatized with 3-(2-pyridyldithio) propionic acid N-hydroxysuccinimide ester (Sigma), a bifunctional crosslinker, at 10 μg/ml for 30 min at room temperature, and then a solution containing the reduced peptide was added to the wells at different concentrations and allowed to react for at least 1 hr. (The crosslinker reacts mainly with amino groups in the albumin and subsequently crosslinks the peptide to albumin through the cysteine residue in the peptide.) After repeated washing to remove unattached peptide the plates were used for cell attachment assays. Cell attachment in wells coated directly with the peptides was compared with that seen in wells containing albumin-linked peptides, albumin-linked fibronectin, fibronectin alone, or derivatized albumin alone.

Coupling of Peptides to Sepharose Beads. The four synthetic peptides as well as the 11.5-kDal fragment and a 200-kDal fragment of fibronectin were coupled to cyanogen bromide-activated Sepharose-6MB beads (Pharmacia) according to the manufacturer's instructions. The peptides were first reduced as described above and used at 8 mg of peptide per ml of Sepharose. Albumin-coated beads and beads derivatized with ethanolamine were used as controls.

Cell Attachment Assay. The cell attachment assays were performed as described (Ruoslahti, E. et al. (1981) *Methods Enzymology* 82, 803–831) with human fibroblasts or normal rat kidney (NRK) cells. Briefly, 100 1 of a single-cell suspension containing 10 cells was placed in a flat-bottom microtiter well that had been coated with one of the peptides or with fibronectin. After 1 hr at 37 C., unattached cells were washed away and attached cells were fixed and stained for counting. In some experiments soluble peptide was added to the medium to determine if its presence during the attachment would have an inhibitory effect. Cell attachment to the agarose beads was performed on a layer of beads in the bottom of a round-bottom microtiter well exactly as described above.

Iodination of Peptides. The well-known chloramine-T method was used to label 50 g of peptides II, III, and IV each with 0.33 mCi (1 Ci=3.7×10 Bq) of I. Uncoupled iodide was removed and quantitated by passage through a column of Sephadex G-25.

RESULTS

The four synthetic peptides studied for their effect on cell attachment are shown in FIG. 1. Some degree of overlap was included to avoid the possibility of splitting, and thereby losing, the cell recognition site. The peptides were allowed to adsorb directly to polystyrene microtiter wells or were attached to albumin-coated polystyrene via their COOH-terminal cysteine residue by using a bifunctional crosslinker. Surfaces derivatized in this manner were then tested for their ability to support the attachment of cells. FIG. 2 shows the results of such experiments.

Peptide IV, which consists of the COOH-terminal 30 amino acids of the 11.5-kDal cell attachment fragment of fibronectin (plus a cysteine residue), supported the attachment of both NRK cells and human fibroblasts whether coupled to albumin or adsorbed directly to the surface. Coupling to albumin, however, greatly increased the activity of this peptide. When coupled to albumin, as little as 20 ng of peptide IV could be detected per microtiter well (see FIG. 2). Peptides I, II, and III, on the other hand, had no activity in this assay. The activity of whole fibronectin was independent of the pretreatment of the substrate with the crosslinker-derivatized albumin. Because the binding curves for fibronectin were similar whether the protein was bound to plastic directly or via albumin, only the data obtained by using plastic-bound fibronectin are shown.

To confirm that the lack of activity of the inactive peptides was not due to a lack of binding to the polystyrene surface, peptides II, III, and IV were radioiodinated and incubated overnight in microtiter wells. FIG. 3 shows that all three peptides bind to the microtiter wells to similar extents. Peptide IV bound slightly less well than the others, possibly because, of the four peptides, it is the most hydrophilic. The binding of all three peptides to polystyrene could be inhibited by the corresponding unlabeled peptide, indicating that radioiodination had not altered their capacity to bind to this type of surface. Furthermore, cells attached to $^{125}I$-labeled peptide IV in a dose-dependent manner identical to that seen with unlabeled peptide. Tests were conducted to determine whether the presence of peptide IV in a soluble form would inhibit the adhesion of cells to microtiter wells coated with this peptide or with fibronectin. At concentrations up to 150 μg/ml, however, peptide IV had no effect on the attachment of cells to these surfaces after 1 hour.

To confirm the specificity of the activity found in peptide IV, all of the peptides were coupled to cyanogen bromide-activated Sepharose 6MB. The efficiency of coupling of all four peptides was greater than 90% as judged on the basis of UV absorbance. Beads to which peptide IV was coupled supported attachment of cells, as did beads with the entire 11.5-kDal fragment or a 200-kDal fragment of fibronectin. The latter fragment was used instead of intact fibronectin because of the greater stability and higher biological activity of beads coated with fragments. Agarose beads derivatized with ethanolamine or with albumin were devoid of cell attachment activity, as were beads having peptides I, II, or III on their surfaces.

The data show that most, if not all, of the cell attachment activity of fibronectin can be accounted for by 30 amino acid residues. Because this is only about 1% of the intact fibronectin polypeptide monomer, an extremely specific interaction between the cell surface and this portion of the fibronectin molecule can be inferred. The active peptide, peptide IV, is the most hydrophilic of the four synthetic peptides constituting the cell attachment domain of fibronectin, whereas peptides II and III are quite hydrophobic and peptide I has intermediate characteristics. This probably results in the 30 residues of peptide IV being exposed on the surface of the corresponding portion of the intact fibronectin molecule and is consistent with the presence of the activity in this part of the fragment.

It is important to note that peptide IV was active on three different types of surfaces, including the hydrophobic polystyrene surface and the hydrophilic Sepharose beads. This makes it unlikely that we would be dealing with some kind of nonspecific modification of the surface that would make it more attractive to cells. This argument is further strengthened by the fact that we could show that the binding of the different peptides to these surfaces was similar, yet only peptide IV was effective in cell attachment. Furthermore, this peptide had a high specific activity. When crosslinker-derivatized albumin was used to mediate the binding of the peptides to the polystyrene surface, peptide IV was nearly as active on a molar basis as intact fibronectin itself. When peptide IV was used to coat polystyrene microtiter wells directly, however, about 10 times the molar amount was required to obtain the same effect as was seen with intact fibronectin in inducing cell attachment. This could be due to loss of function as a result of binding, or it may reflect a relative inefficiency or reversibility of the binding of this peptide to polystyrene compared to the larger fibronectin molecule.

The nature of the component(s) (receptor) at the cell surface that interacts with the cell attachment site of fibronectin is not known. The data presented here strongly suggest that a discrete cell surface receptor, or class of receptors, exists. The synthetic peptide, or shorter derivatives of it if active, could be helpful in identifying this receptor. One can predict a turn in the peptide chain in the hydrophilic area around the proline residue number 10 in peptide IV. This could result in a loop available for interaction with cells. Subsequent experiments confirmed this result, as discussed hereinafter.

For reasons that are incompletely understood, expression of the cell attachment function of fibronectin requires that fibronectin is presented to cells bound to a solid phase such as a plastic surface or a collagen matrix, whereas soluble fibronectin does not bind detectably to cells. Peptide IV behaves similarly, in that soluble peptide IV did not inhibit the attachment of cells to immobilized peptide IV or fibronectin. It is likely that a cooperative binding of the cell surface with several fibronectin molecules is required for a productive interaction. It may be possible to construct an analog(s) of this peptide that would bind more strongly to the cell surface. Not only would this facilitate the identification of the cell surface receptor for fibronectin, but also it might allow the modulation of cell attachment.

Practical application such as the preparation of surfaces for optimal cell culture and derivatization of various prosthetic materials to promote bonding with surrounding tissues can also be envisioned. Since a peptide of 30 amino acids is unlikely to have more than one binding site, one question that can be addressed now is whether the interaction of all types of cells with fibronectin involves this same region of the molecule. Platelets, for example, may bind fibronectin on their surfaces by a different mechanism. This would be an important detail in using this peptide to regulate cell attachment or in the design of prosthetic materials. It would also shed light on the role played by fibronectin in vivo.

INDUSTRIAL APPLICATION

Coating of the culture substratum with the cell-attachment polypeptide obviates the use of fibronectin in the medium, thus providing better defined conditions for the culture as well as better reproducibility. As one example of commercial use of cell-attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of fibronectin in the growth medium, and the cell-attachment polypeptide is expected to provide an improved, chemically-defined coating for such purposes.

Medical devices can be designed making use of such substrata to attract cells to the surface in vivo or even to promote the growing of a desired cell type on a particular surface prior to grafting. An example of such an approach is the induction of endothelial cell growth on a prosthetic blood vessel or vacular graft, which is generally woven or knitted from polyester fiber, particularly Dacron fiber (a polyethylene terephthalate). Most types of cells are attracted to fibronectin and to this polypeptide, but endothelial cells and fibroblastic cells in particular are attracted to fibronectin. The latter point indicates the potential usefulness of this defined polypeptide in coating a patch graft or the like for aiding wound closure and healing following an accident or surgery. In such cases, it may be advantageous to couple the peptide to a biological molecule, such as collagen, a glycosaminoglycan or a proteoglycan; for example, the 30-residue fragment having a Cys-residue at the C-terminus coupled to monomeric collagen. This can be achieved by using a crosslinker such as 3-(2-Pyridyldithio) propionic Acid N-Hydroxysuccinimide Ester to effect cross-linking of the cysteine to a lysine residue in the collagen. It is also indicative of its value in coating surfaces of a prosthetic device which is intended to serve as a temporary or semipermanent entry into the body, e.g. into a blood vessel or into the peritoneal cavity, sometimes referred to as a percutaneous device. The invention may be in the form of a liquid, such as eye drops or lotions, for example, or a salve or gel which may be applied to promote cell attachment, or in any other convenient form. Fibronectin has been shown to be chemotactic to fibroblast and macrophages. This activity correlates with the presence of the cell attachment domain. One manifestation of the cell attachment activity of the synthetic peptides described here, and fragments thereof of like characteristics, is chemotactic activity.

Although the invention has been described with regard to certain preferred embodiments, it should be understood that various changes and modifications, as would be obvious to one having the ordinary skill in this art, may be made without departing from the scope of the invention which is defined in the appended claims. For example, it may not be necessary to have the free acid at the C-terminus, as it may be amidated or substituted by some other group. Particular features of the invention are emphasized in the claims which follow.

What is claimed is:

1. The biologically active amino acid polymer consisting essentially of the polypeptide: Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-R-OH.

2. A composition of matter consisting essentially of an amino acid polymer which is biologically active, exhibits cell attachment activity and is characterized as a substantially isolated polypeptide having the formula: Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-R-OH.

3. A prosthetic device having a biologically active surface which exhibits cell attachment activity, said surface having linked thereto a biologically active amino acid polymer: Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-R-OH.

4. A polypeptide in accordance with claim 1 wherein R is Cys.

5. A polypeptide in accordance with claim 1 wherein R is des-R.

6. A polypeptide in accordance with claim 1 coupled to collagen.

7. A prosthetic device in accordance with claim 3 wherein R is Cys.

8. A prosthetic device in accordance with claim 3 wherein R is des-R.

9. A prosthetic device in accordance with claim 3 wherein said surface constitutes a portion of a vascular graft.

10. A prosthetic device in accordance with claim 3 wherein said surface is made of asynthetic resin fiber.

11. A prosthetic device in accordance with claim 3 wherein said surface constitutes a portion of a percutaneous device.

* * * * *